United States Patent [19]

Doria et al.

[11] 4,152,449
[45] May 1, 1979

[54] 2-VINYL-CHROMONES AND PHARMACEUTICALS THEREWITH

[75] Inventors: Gianfederico Doria, Milan; Ciriaco Romeo, Serino; Francesco Lauria, Milan; Maria L. Corno, Milan; Piernicola Giraldi, Milan; Marcello Tibolla, Canale d'Agordo, all of Italy

[73] Assignee: Carlo Erba S. p. A., Milan, Italy

[21] Appl. No.: 803,947

[22] Filed: Jun. 6, 1977

[30] Foreign Application Priority Data

Jun. 16, 1976 [IT] Italy .............................. 24356A/76
Jan. 12, 1977 [IT] Italy .............................. 19193 A/77

[51] Int. Cl.² .................... A61K 31/35; C07D 407/06
[52] U.S. Cl. .................................. 424/283; 424/275; 542/441
[58] Field of Search ............... 542/441; 260/345.2; 424/275, 283

[56] References Cited

U.S. PATENT DOCUMENTS

| | | | |
|---|---|---|---|
| 3,470,165 | 9/1969 | Fitzmaurice | 542/441 |
| 3,816,466 | 6/1974 | Strandtmann et al. | 260/345.2 |
| 3,896,114 | 7/1975 | Nohara et al. | 542/441 |
| 3,993,669 | 11/1976 | Pfister | 260/345.2 |
| 4,033,845 | 7/1977 | Cohen et al. | 542/441 |

FOREIGN PATENT DOCUMENTS

781467 3/1968 Canada ..................................... 542/441

OTHER PUBLICATIONS

Shah et al., J. Am. Chem. Soc. 77 (1955) pp. 2223–2224.
Koo, J. Org. Chem. 26 (1961) pp. 2440–2442
Renzi, Chem. Abst. 67 (1967) #64296s.

*Primary Examiner*—Allen B. Curtis
*Attorney, Agent, or Firm*—Murray & Whisenhunt

[57] ABSTRACT

Substituted 2-vinyl-chromones are disclosed wherein the chromone ring has an alkyl or alkenyl substituent at the 3-position. The compounds exhibit anti-allergy activity and can be used to treat allergic conditions.

11 Claims, No Drawings

2-VINYL-CHROMONES AND PHARMACEUTICALS THEREWITH

The present invention relates to substituted 2vinyl-chromones, to a process for their preparation and to pharmaceutical compositions containing them.

The compounds of the invention have the following formula (I)

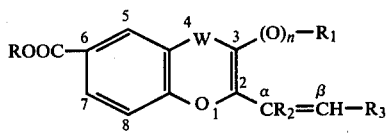

wherein
n is zero or 1;
R is hydrogen or $C_1$–$C_{12}$ alkyl, unsubstituted or substituted by a $C_2$–$C_5$ alkanoyloxy or by a

group, wherein each of $R_4$ and $R_5$ is independently selected from the group consisting of hydrogen and $C_1$–$C_{10}$ alkyl;
$R_1$ is $C_2$–$C_4$ alkyl or $C_3$–$C_4$ alkenyl;
$R_2$ is hydrogen or methyl;
$R_3$ is (a) furyl, thienyl or pyridyl, being the furyl, thienyl and pyridyl groups unsubstituted or substituted by a methyl group; or (b) the group

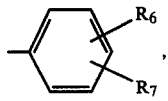

wherein each of $R_6$ and $R_7$ is independently selected from the group consisting of (a') hydrogen; (b') halogen; and (c') the group $-(O)_{n_1} - R_8$, wherein $n_1$ is zero or 1 and $R_8$ is $C_3$–$C_4$ alkenyl or $C_1$–$C_4$ alkyl, being the alkenyl and the alkyl groups unsubstituted or substituted by one or more $C_1$–$C_2$ alkoxy or hydroxy groups;
W is $>C=O$ or $>C=S$.

Object of the present invention are also the pharmaceutically acceptable salts of the compounds of formula (I), as well as all the possible isomers and the mixtures thereof.

In the compounds of the invention the vinyl moiety may be either in the cis- or in the trans-configuration, that is the substituent $R_2$ on the $\alpha$ carbon atom and the hydrogen on the $\beta$ carbon atom may be on the same side or on the opposite sides in respect of the vinylic double bond. Also the mixture of the cis- and trans-isomers is included in the scope of the present invention. Preferably, in the compounds of the invention, the vinyl moiety has the trans-configuration.

The numbering used to identify the position of the substituents in the $R_3$ radical is the conventional one, as is shown by the following examples:

(a) when $R_3$ is phenyl:

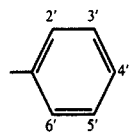

(b) when $R_3$ is pyridyl:

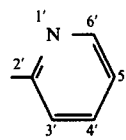 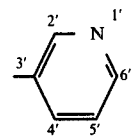 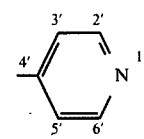

(c) when $R_3$ is furyl or thienyl:

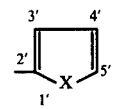

wherein X is oxygen or sulphur. The alkyl, alkenyl, alkoxy and alkanoyloxy groups may be branched or straight chain groups. When R is an unsubstituted $C_1$–$C_{12}$ alkyl, it is preferably $C_1$–$C_6$ alkyl, in particular methyl, ethyl, isopropyl, t-butyl and hexyl. When R is a $C_1$–$C_{12}$ alkyl substituted by $C_2$–$C_5$ alkanoyloxy, R is preferably pivaloyloxymethyl. When $R_4$ and/or $R_5$ are $C_1$–$C_{10}$ alkyl, the alkyl group is preferably $C_1$–$C_4$ alkyl, in particular methyl, ethyl, isopropyl and t-butyl. $R_1$ is preferably $C_2$–$C_3$ alkyl, in particular ethyl and propyl or $C_3$ alkenyl, in particular allyl. When $R_3$ is furyl, thienyl or pyridyl, it is preferably 2-furyl, 2-thienyl or 2-pyridyl. When $R_8$ is $C_1$–$C_4$ alkyl, it is preferably methyl or ethyl. Preferably $R_6$ and $R_7$ are independently selected from the group consisting of hydrogen, methoxy, methyl and ethyl. Examples of pharmaceutically acceptable salts are either those with inorganic bases, such as sodium, potassium, calcium and aluminium hydroxides or with organic bases, such as lysine, triethylamine, triethanolamine, dibenzylamine, methylbenzylamine, di-(2-ethyl-hexyl)-amine, piperidine, N-ethyl-piperidine, N,N-diethylaminoethylamine, N-ethylmorpholine, β-phenethylamine, N-benzyl-β-phenethylamine, N-benzyl-N,N-dimethylamine and the other acceptable organic amines, as well as the salts with inorganic, e.g. hydrochloric, hydrobromic and sulphuric, acids and with organic acids, e.g. citric, tartaric, maleic, malic, fumaric, methanesulphonic and ethanesulphonic acids. Preferred salts are the sodium and potassium salts, as well as the hydrochlorides of the basic esters, e.g. the diethylaminoethyl and dimethylaminoethyl esters. Particularly preferred compounds of the invention are those of formula (I) wherein R is hydrogen or unsubstituted $C_1$–$C_6$ alkyl, $R_1$ is ethyl, propyl or allyl, $R_2$ is hydrogen or methyl, $R_3$ is (a) a phenyl group, unsubstituted or substituted by one or two methyl, ethyl or methoxy groups or (b) 2-furyl, 2-thienyl or 2-pyridyl, being the furyl, the thienyl and the pyridyl groups unsubstituted or substituted by a methyl group, and W is $>C=O$ and wherein the vinyl moiety has the trans-configuration, as well as their pharmaceutically acceptable salts.

Examples of particularly preferred compounds of the invention are:
6-carboxy-3-ethyl-2-trans-styryl-chromone;
6-carboxy-3-allyl-2-trans-styryl-chromone;

6-carboxy-3-propyl-2-trans-styryl-chromone;
6-carboxy-3-propyl-2-trans-(2'-methyl-styryl)-chromone;
6-carboxy-3-propyl-2-trans-(3'-methyl-styryl)-chromone;
6-carboxy-3-propyl-2-trans-(4'-methyl-styryl)-chromone;
6-carboxy-3-propyl-2-trans-(2',5'-dimethyl-styryl)-chromone;
6-carboxy-3-propyl-2-trans-[β-(2'-thienyl)-vinyl]-chromone;
6-carboxy-3-propyl-2-trans-[β-(2'-furyl-5'-methyl)-vinyl]-chromone;
6-carboxy-3-propyl-2-trans-[β-(2'-thienyl-5'-methyl)-vinyl]-chromone;
6-carboxy-3-propyl-2-trans-[β-(2'-pyridyl-6'-methyl)-vinyl]-chromone;
6-carboxy-3-ethyl-2-trans-[β-(2'-pyridyl-6'-methyl)-vinyl]-chromone;
6-carboxy-3-ethoxy-2-trans-styryl-chromone;
6-carboxy-3-ethoxy-2-trans-(2'-methyl-styryl)-chromone;
6-carboxy-3-ethoxy-2-trans-[β-(2'-thienyl)-vinyl]-chromone;
6-carboxy-3-ethoxy-2-trans-[β-(2'-pyridyl-6'-methyl)-vinyl]-chromone;
6-carboxy-3-ethoxy-2-trans-[β-(2'-furyl-5'-methyl)-vinyl]-chromone, as well as the pharmaceutically acceptable salts thereof, in particular, the sodium salt and the hydrochlorides of the basic esters (e.g. of those with diethylaminoethanol and dimethylaminoethanol) and the $C_1$–$C_6$ alkyl esters thereof, in particular the ethyl, isopropyl, t-butyl and hexyl esters. The compounds of the invention are prepared by a process comprising:

(a) cyclizing a compound of formula (II)

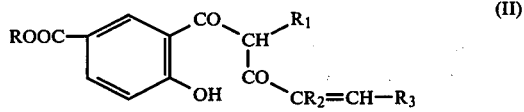   (II)

wherein R, $R_1$, $R_2$ and $R_3$ are as defined above, so obtaining compounds of formula (I), wherein n is zero and W is $>C=O$; or (b) reacting a compound of formula (III)

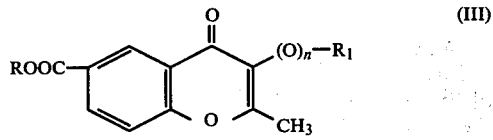   (III)

wherein n, R and $R_1$ are as defined above, with an aldehyde of formula (IV)

   (IV)

OHC—$R_3$ wherein
$R_3$ is as defined above, so obtaining compounds of formula (I) wherein
$R_2$ is hydrogen, W is $>C=O$, and the vinyl moiety has the trans-configuration; or (c) alkylating a compound of formula (V)

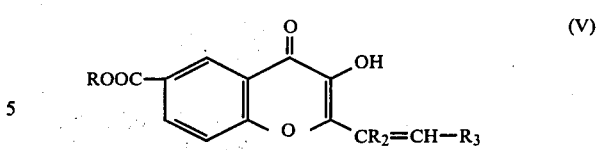   (V)

wherein R, $R_2$ and $R_3$ are as defined above, so obtaining compounds of formula (I) wherein n is 1 and W is $>C=O$; and, if desired, converting a compound of formula (I) wherein W is $>C=O$ into a compound of formula (I) wherein W is $>C=S$ and/or, if desired, converting a compound of formula (I) into another compound of formula (I) by known methods and/or, if desired, converting a compound of formula (I) into a pharmaceutically acceptable salt and/or, if desired, converting a salt into a free compound and/or, if desired, separating a mixture of isomers into the single isomers.

The cyclisation of the compound of formula (II) may be preferably performed in the presence of an acid catalyst, such as, for example, hydrochloric acid, hydroiodic acid, sulphuric acid or formic acid, at a temperature ranging preferably between 20° C. and 120° C.; the cyclisation reaction is preferably carried out in an inert organic solvent selected, e.g., from the group consisting of methanol, ethanol, dioxane, tetrahydrofuran, benzene, toluene, acetic acid and their mixtures.

The reaction of the compound of formula (III) with the aldehyde of formula (IV) is preferably carried out in the presence of basic condensing agents, such as, for example, sodium ethoxide, sodium methoxide, sodium hydroxide, sodium hydride, sodium amide, in a solvent selected, e.g., from the group consisting of methanol, ethanol, dioxane, water and their mixtures, at a temperature preferably ranging between about 0° C. and 120° C.

The alkylation of the compound of formula (V) is preferably carried out in a conventional manner, for example, by reacting a compound of formula (V) with an alkyl or alkenyl halide of formula $R_1$-Z, wherein $R_1$ is as defined above and Z is chlorine, bromine or iodine, in an inert solvent such as acetone, dioxane, dimethylformamide, hexamethylphosphorotriamide in the presence of a basic agent such as, for example, sodium amide, sodium hydride, sodium methoxide, sodium or potassium carbonate, at a temperature ranging between about 0° C. and about 150° C.

A compound of formula (I) wherein W is $>C=O$ may be converted into a compound of formula (I) wherein W is $>C=S$ by reaction, e.g., with $P_2S_5$ in an inert solvent, such as benzene, toluene, xylene, pyridine at a temperature ranging from the room temperature to about 150° C.

A compound of formula (I) may be converted, as stated above, into another compound of formula (I) by known methods.

For example, a compound of formula (I) wherein COOR is an esterified carboxy group, may be converted into a compound of formula (I) wherein COOR is carboxy, by basic hydrolysis, using, e.g., sodium or potassium hydroxide, in a solvent, such as water or a lower aliphatic alcohol, and operating at a temperature ranging from the room temperature to about 150° C.; the same reaction may be also carried out by treatment with lithium bromide in dimethylformamide at a temperature higher than 50° C.

A compound of formula (I) wherein COOR is carboxy may be converted into a compound of formula (I) wherein COOR is an esterified carboxy group, e.g., a carbalkoxy group, by reaction, for example, of the alkaline salt of the acid with the suitable alkyl halide, in an inert solvent, such as acetone, dioxane, dimethylformamide, hexamethylphosphorotriamide at a temperature ranging from about 0° C. to about 100° C.

Also the optional salification of a compound of formula (I) as well as the conversion of a salt into the free compound and the separation of a mixture of isomers into the single isomers may be carried out by conventional methods. For example the separation of a mixture of optical antipodes into the single antipodes may be carried out by salification with an optically active base and by subsequent fractionated crystallization. So the separation of an eventual mixture of cis- and trans- geometric isomers may be carried out, for example, by fractionated crystallization.

The compounds of formula (II) may be prepared by reacting a compound of formula (VI)

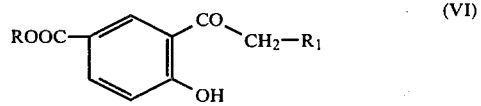

wherein

R and $R_1$ are as defined above, with a compound of formula (VII)

$$ZOC-CR_2=CH-R_3 \qquad (VII)$$

$R_2$, $R_3$ a d Z are as defined above, by conventional methods, e.g., operating in an inert solvent such as benzene, toluene, dioxane at a temperature ranging from 0° C. to the reflux temperature, in the presence of a basic agent, such as pyridine, triethylamine, as acid acceptor, so obtaining a compound of formula (VIII)

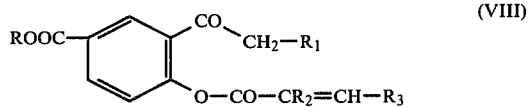

wherein

R, $R_1$, $R_2$ and $R_3$ are as defined above and then submitting the compound of formula (VIII) to a rearrangement to give the compounds of formula (II); the rearrangement is carried out in an inert solvent, for example, pyridine,, toluene, methyl-ethyl-ketone, or isopropyl alcohol, in the presence of a strong base, e.g., sodium, sodium amide, potassium or sodium hydroxide, or potassium carbonate, at a temperature ranging from the room temperature to the reflux temperature.

An alternative method to prepare the compounds of formula (II) is the reaction of a compound of formula (IX)

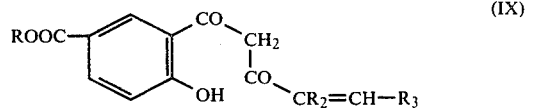

wherein

R, $R_2$ and $R_3$ are as defined above, with a suitable alkyl or alkenyl halide of formula $R_1-Z$, wherein $R_1$ and Z are as defined above, in a solvent such as, for example, dioxane, dimethylformamide, hexamethylphosphorotriamide and their mixtures in the presence of sodium or potassium carbonate, at a temperature ranging from the room temperature to about 150° C.

The compounds of formula (III) may be prepared by known methods, for example, by reacting a compound of formula (VI) with an excess of acetic anhydride at a temperature ranging from the room temperature to the reflux temperature, so obtaining compounds of formula (III) wherein n is zero.

Alternatively the compounds of formula (III) may be prepared by reacting a compound of formula (X)

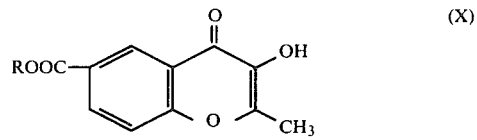

wherein

R is as defined above with a suitable alkyl or alkenyl halide of formula $R_1$-Z, wherein $R_1$ and Z are as defined above, in a solvent such as acetone, dioxane, dimethylformamide in the presence of a basic agent such as sodium hydride, sodium methoxide, sodium or potassium carbonate, at a temperature ranging from the room temperature to about 120° C., so obtaining compounds of formula (III) wherein n is 1.

The compounds of formula (IV) are commercially available products. The compounds of formula (V) may be prepared, for example, by reacting a compound of formula (X) with an aldehyde of formula (IV) following the reaction conditions used in the reaction of the compound of formula (III) with the compound of formula (IV), so obtaining compounds of formula (V) wherein $R_2$ is hydrogen, and the vinyl moiety has the trans-configuration.

Alternatively the compounds of formula (V) may be prepared by cyclisation of a compound of formula (XI).

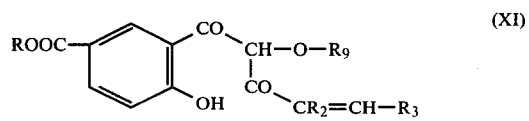

wherein

R, $R_2$ and $R_3$ are as defined above and $R_9$ is hydrogen or a lower alkanoyl group, preferably acetyl; the cyclisation is carried out by using the same reaction conditions employed in the cyclisation of the compound of formula (II).

The compounds of formula (V) may also be prepared by reacting a compound of formula (XII)

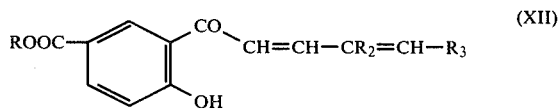

wherein

R, $R_2$ and $R_3$ are as defined above, with hydrogen peroxide in a basic medium, such as, for example, sodium methoxide, sodium ethoxide, sodium or potassium hydroxide in methanol, ethanol, water and their mixtures, at a temperature ranging from 0° C. to the reflux temperature.

The compounds of formula (VI) may be prepared from the corresponding phenoxy derivatives, which are known compounds, by Fries rearrangement.

The compounds of formula (VII) are known compounds and they may be prepared by conventional methods.

The compounds of formula (IX) may be prepared by reacting the compound of formula (VI) wherein $R_1$ is hydrogen, with a compound of formula (VII), using the same reaction conditions employed for the preparation of the compound of formula (II).

The compounds of formula (X) may be prepared, for example, by acid hydrolysis of a compound of formula (XIII).

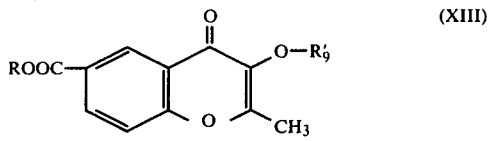

wherein

R is as defined above and $R_9'$ is lower alkanoyl, e.g., acetyl, which in turn, may be prepared by reacting a compound of formula (XIV)

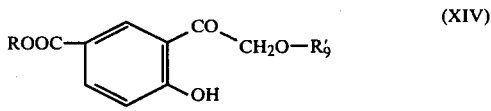

wherein R is as defined above and $R_9'$ is as defined above, with an excess of acetic anhydride at a temperature ranging from the room temperature to the reflux temperature.

The compounds of formula (XI) may be prepared according to the method above described for the synthesis of the compounds of formula (II), starting from a compound of formula (XIV).

The compounds of formula (XII) may be prepared, for example, by reacting a compound of formula (XV)

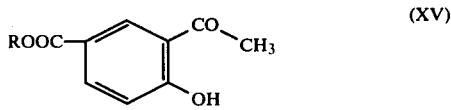

wherein

R is as defined above, with an aldehyde of formula (XVI)

$$OHC-CR_2=CH-R_3 \quad (XVI)$$

wherein $R_2$ and $R_3$ are as defined above, in a solvent such as methanol, ethanol, dioxane, water and their mixtures in the presence of a basic condensing agent such as sodium ethoxide, sodium or potassum hydride, sodium or potassium carbonate, at a temperature ranging from 0° C. to the reflux temperature.

The compounds of formula (XIV) may be prepared, for example, by reacting a compound of formula (XVII)

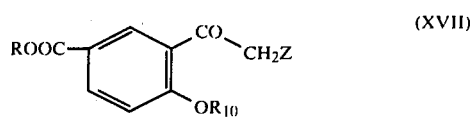

wherein

R and Z are as defined above and $R_{10}$ is a known protecting group, such as, for example, a benzyl group, with an alkaline, e.g. sodium or potassium, salt or with a triethylamine salt of a compound of formula $R_9'$—OH, wherein $R_9'$ is as defined above, in a solvent such as acetone, dioxane, dimethylformamide and acetic acid at a temperature ranging from 0° C. to about 100° C., so obtaining a compound of formula (XVIII)

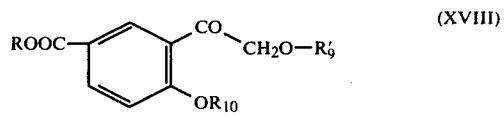

wherein

R, $R_9'$ and $R_{10}$ are as defined above, and then removing the protecting group, if desired, by conventional methods, e.g., by acid hydrolysis or by hydrogenolysis, in the specific case of a benzyl moiety.

The compounds of formula (XVII) may be prepared by halogenation of a compound of formula (XIX)

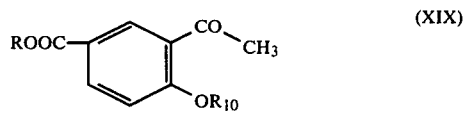

wherein

R and $R_{10}$ are as defined above, using conventional methods, e.g., by reacting with chlorine or bromine in an inert solvent such as $CH_2Cl_2$, $CCl_4$, acetic acid pyridine, at a temperature varying between 0° C. and 30° C. or with $CuBr_2$ in chloroform-ethyl acetate at the reflux temperature.

In the compounds of formulae (II), (V), (VII), (VIII), (IX), (XI), (XII), and (XVI) the vinyl group may have either the cis- or the trans-configuration, although it has preferably the trans-configuration.

The compounds the invention own anti-allergic activity, as is shown by the fact that they are active in the passive cutaneous anaphylaxis (PCA) test in rats, according to Goose J. And Blair A.M.J.N. (Immunology, 16, 749, 1969). They can be therefore used in prevention and treatment of bronchial asthma, allergic rhinitis, hay fever, urticaria and dermatosis.

Furthermore, the compounds of the invention offer the important advantage of being highly active as anti-allergic agents also when orally administered, as is shown by the following Table, where the potency ratios of some compounds of the invention are reported with respect to the compound 6-carboxy-2-transtyryl-chromone (K 10210), i.e. the most active compound of the vinylic series described in Belgian Pat. No. 823,875 (claiming the priorities of the Italian Patent applications Nos. 32089 A/73, 24777 A/74 and 25244 A/74), partially corresponding to U.S. application No. 691,489 filed on June 1, 1976). To the anti-allergic activity of the compound 6-carboxy-2-trans-styryl-chromone the conventional value 1 was given.

TABLE

| Compound | Potency ratios (K 10210 = 1) | Fiducial limits for P = 0.95 |
|---|---|---|
| 6-carboxy-3-ethyl-2-trans-styryl-chromone | 19.85 | (13.999–29.133) |
| 6-carboxya-3-propyl-2-trans-styryl-chromone | 27.95 | (19.316–42.308) |
| 6-carboxy-3-allyl-2-trans-styryl-chromone | 29.90 | (20.038–47.828) |
| 6-carboxy-3-propyl-2-trans-(2'-methyl-styryl)-chromone | 78.48 | (47.174–144.857) |
| 6-carboxy-3-ethoxy-2-trans-styryl-chromone | 20.96 | (13.851–32.890) |
| 6-carboxy-3-propyl-2-trans-[β-(2'-thienyl)-vinyl]-chromone | 23.19 | (14.554–38.654) |

The anti-allergic activity was determined by the inhibition of the IgE-mediated PCA according to Goose J. and Blair A.M.J.N. (loc.cit.) using homocytotropic antibodies raised in rates following the method of Mota I., Immunology, 7, 681 (1964). The tested compounds were administered per os 15 minutes before the administration of the antigen at 3 or more dosage levels. At least 8 rats were used per each dose.

The potency ratios were calculated according to the method of Finney, D. J. (1952) Statistical Method in Biological Assay, C. Griffin London, page 118.

It is interesting to note that the anti-allergic activity of the compounds of this series is strictly connected with the number of carbon atoms in the $R_1$ radical. In fact, for instance, the compounds wherein the $R_1$ radical contains at least two carbon atoms, are much more potent than their lower analogues.

For example the compound 6-carboxy-3-ethyl-2-trans-styryl-chromone is about 5.5 times more potent than the corresponding 3-methyl-derivative and the compound 6-carboxy-3-propyl-2-trans-chromone is about 7.5 times more potent than the same 3-methyl-derivative.

Furthermore, the compounds of the invention possess also spasmolytic activity, in particular brochodilator activity, which is useful in the treatment, for example, of bronchial asthma.

The compounds of the invention may be administered in a conventional manner, for instance, orally and parenterally at a daily dosage preferably of 0.25 to 15 mg/kg, or by inhalation, preferably at a daily dosage of 1.25 to 100 mg, preferably 0.5 to 25 mg, or by topical application.

The nature of the pharmaceutical compositions containing the compounds of this invention in association with pharmaceutically acceptable carriers or diluents will, of course, depend upon the desired mode of administration.

The compositions may be formulated in the conventional manner with the usual ingredients. For example, the compounds of the invention may be administered in the form of aqueous or oily solutions or suspensions, aerosols, as well as powders, tablets, pills, gelatine capsules, syrups, or creams, or lotions for topical use.

Thus, for oral administration, the pharmaecutical compositions containing the compounds of this invention, are preferably tablets, pills or gelatine capsules which contain the active substance together with diluents, such as, for example, lactose, dextrose, sucrose, manitol, sorbitol, cellulose; lubricants, for instance, silica, talc, stearic acid, magnesium or calcium stearate, and/or polyethylene glycols; or they may also contain binders, such as, for example, starches, gelatine, methyl-cellulose, carboxymethylcellulose, gum-arabic, tragacanth, polyvinylpyrrolidone, disintegrating agents, such as, for instance, starches, alginic acid, alginates, sodium starch glycolate; effervescing mixtures; dye-stuffs; sweeteners; wetting agents, such as, for instance, lecithin, polisorbates, laurylsulphates; and, in general, non-toxic and pharmacologically inactive substances used in pharmaceutical formulations. Said pharmaceutical preparations may be manufactured in known manner, for example, by means of mixing, granulating, tabletting, sugar-coating, or film-coating processes. For the treatment of allergic asthma, the compounds of the invention are also administered by inhalation. For such use, suitable compositions may comprise a suspension or solution of the active ingredient, preferably in the form of a salt, such as the sodium salt, in water, for administration by means of a conventional nebulizer. Alternatively, the compositions may comprise a suspension or a solution of the active ingredient in a conventional liquified propellant, such as, dichlorodifluoromethane or dichlorotetrafluoroethane to be administered from a pressurized container, i.e., an aerosol dispenser. When the medicament is not soluble in the propellant, it may be necessary to add a co-solvent, such as, ethanol, dipropylene glycol, isopropyl myristate, and/or a surface-active agent to the composition, in order to suspend the medicament in the propellant medium and such surface-active agents may be any of those commonly used for this purpose, such as non-ionic surface-active agents, e.g., lecithin. The compounds of the invention may also be administered in the form of powders by means of a suitable insufflator device and in this case the fine particle sized powders of the active ingredient may be mixed with a diluent material such a lactose.

Furthermore, the compounds of this invention may also be adminisered by intradermal or intravenous injection in the conventional manner.

In addition to the internal administration, the compounds of this invention may find use in compositions for topical application, e.g. as creams, lotions or pastes for use in dermatological treatments. For these compositions the active ingredient may be mixed with conventional oleaginous or emulsifying excipients.

The following examples illustrate but do not limit the present invention.

EXAMPLE 1 g 14 of methyl 3-butyryl-4-hydroxy-benzoate (m.p. = 54–55° C.) dissolved in dioxane (80 ml) containing pyridine (20 ml) were reacted with trans-cinnamoyl chloride at room temperature for 20 hours. The reaction mixture was diluted with water, acidified to pH 4 with 23% HCl and extracted with ethyl acetate. the separated organic phase was washed with 5% $NaHCO_3$ and water and then evaporated to dryness. The obtained residue (24 g) was dissolved in methyl-ethyl-ketone (240 ml), anhydrous $K_2CO_3$ (62 g) was added and the mixture was vigorously stirred under reflux for 3 hours. After cooling the mixture was diluted with cyclohexane (250 ml) and filtered. The collected product was dissolved in water and precipitated by the addition of an excess of 20% citric acid.

After filtration, washing with water and drying, crude 1-(2-hydroxy-5-carbomethoxy-benzoyl)-1-trans-cinnamoyl-propane (17.8 g) was obtained, which was dissolved in 99% formic acid (50 ml) and heated under reflux for 20 minutes. After cooling the mixture was diluted with ice-water and filtered. After crystallization from ethanol, 6-carbomethoxy-3-ethyl-2-trans-styryl-chromone (9.7 g), m.p.=194–195° C., NMR (CF$_3$COOD): vinylic protons $\delta_{H\beta}$=7.49(d), $\delta_{H\alpha}$=8.31(d) p.p.m., $J_{H\alpha H\beta}$=15.5 Hz, was obtained and treated with 1% KOH solution (190 ml) in 95% ethanol under reflux for 30 minutes. After cooling, the mixture was acidified with 23% HCl to pH 4 and the precipitate was filtered, washed with ethanol and water until neutral so obtaining 6-carboxy-3-ethyl-2-trans-styryl-chromone (8.4 g), m.p.=282–284° C.; IR:δ(C-H)>C=C<(-trans) 960 cm$^{-1}$; NMR (CF$_3$COOD): vinylic protons $\delta_{H\beta}$=7.43(d),$\delta_{H\alpha}$=8.16(d) p.p.m., $J_{H\alpha H\beta}$=15.5 Hz. By proceeding analogously and starting from the suitable intermediates, the following compounds were obtained:

- 6-carboxy-3-propyl-2-trans-styryl-chromone, m.p.=270–272° C, IR:δ(C-H)>C=C<(trans)955 cm$^{-1}$; NMR (CF$_3$COOD): vinylic protons $\delta_{H\beta}$=7.52(d), $\delta_{H\alpha}$=8.27(d) p.p.m., $J_{H\alpha H\beta}$=15.9 Hz;
- 6-carboxy-3-isopropyl-2-trans-styryl-chromone, m.p.=271°–273° C., IR:δ(C-H)>C=C<(-trans)960 cm$^{-1}$; NMR (CF$_3$COOD): vinylic protons $\delta_{H\beta}$=7.24(d), $\delta_{H\alpha}$=7.64(d) p.p.m., $J_{H\alpha H\beta}$=16 Hz;
- 6-carboxy-3-butyl-2-trans-styryl-chromone, m.p.=261–262° C., IR:δ(C-H)>C=C<(trans)955 cm$^{-1}$;
- 6-carboxy-3-ethyl-2-trans-(2'-methyl-styryl)-chromone, m.p.=270–271°C; NMR (CF$_3$COOD): vinylic protons $\delta_{H\beta}$≡7.27(d), $\delta_{H\alpha}$≡8.38(d) p.p.m., $J_{H\alpha H\beta}$≡16 Hz IRδ(C-H)>C=C<(trans)960 cm$^{-1}$;
- 6-carboxy-3-ethyl-2-trans-(2'-ethyl-styryl)-chromone;
- 6-carboxy-3-butyl-2-trans-(2'-methyl-styryl)-chromone;
- 6-carboxy-3-propyl-2-trans-(2'-methyl-styryl)-chromone, m.p.=234–237° C.; NMR (CF$_3$COOD): vinylic protons $\delta_{H\beta}$=7.34(d), $\delta_{H\alpha}$=8.53(d) p.p.m., $J_{H\alpha H\beta}$=16 Hz; IR: δ(C-H)>C=C<(trans)960 cm$^{31\ 1}$;
- 6-carboxy-3-propyl-2-trans-(4'-methyl-styryl)-chromone, m.p.=266–267° C.;
- 6-carboxy-3-propyl-2-trans-(3'-methyl-styryl)-chromone, m.p.=246–247° C., IR (KBr):δ(C-H) C=C (trans) 960 cm$^{-1}$;
- 6-carboxy-3-ethyl-2-cis-styryl-chromone;
- 6-carboxy-3-propyl-2-cis-styryl-chromone;
- 6-carboxy-3-propyl-2-cis-(2'-methyl-styryl)-chromone.

EXAMPLE 2

By proceeding according to Example 1 and starting from the suitable α-methyl-transcinnamoyl-chlorides, the following compounds were prepared:

- 6-carboxy-3-ethyl-2-trans-(α-methyl-styryl)-chromone, m.p.=193–194° C.; NMR (CF$_3$COOD): vinylic proton $\delta H\beta$=7.13 p.p.m., J(allylic constant)=1.5 Hz;
- 6-carboxy-3-propyl-2-trans-(α-methyl-styryl)-chromone, m.p.=176–178° C.;
- 6-carboxy-3-ethyl-2-trans-(α,2'-dimethyl-styryl)-chromone;
- 6-carboxy-3-propyl-2-trans-(α,2'-dimethyl-styryl)-chromone, m.p.=173–174° C.

EXAMPLE 3 g 64 of methyl 3-valeroyl-4-hydroxy-benzoate(m.p.=78–80° C.) were reacted with acetic anhydride (138 ml) in the presence of triethylamine (38ml) under reflux for 4 hours. After cooling the reaction mixture was diluted with water and ice. The aqueous phase was decanted and the thick oily precipitate was extracted with ethyl acetate. The organic phase was washed with 5% NaHCO$_3$ and water and then evaporated to dryness. The residue, 69.2 g of crude 6-carbomethoxy-3-propyl-2-methyl-chromone, was dissolved in anhydrous methanol (300 ml) and benzaldehyde (58ml) and the solution was slowly added to a solution of sodium (12.4 g) in anhydrous methanol (250 ml). After 20 hours at room temperature, the precipitate was filtered and washed with methanol and water to obtain g 32.5 of 6-carbomethoxy-3-propyl-2-trans-styryl-chromone, m.p.=210°–212° C., which were treated with a 1% KOH solution (600 ml) in 95% ethanol under reflux for 30 minutes. After cooling the mixture was acidified with 23% HCl to pH=4, the precipitate was filtered, washed with ethanol and then with water until neutral so obtaining 6-carboxy-3-propyl-2-trans-styryl-chromone (28 g), m.p.=210°–212° C., IR: δ(C-H)>C=C<(trans)955 cm$^{-1}$; NMR (CF$_3$COOD): vinylic protons $\delta_{H\beta}$=7.52(d), $\delta_{H\alpha}$=8.27(d) p.p.m., $J_{H\alpha H\beta}$=15.9 Hz. By proceeding analogously and starting from the suitable substituted benzaldehydes the following compounds were prepared:

- 6-carboxy-3-propyl-2-trans-(2'-methyl-styryl)-chromone, m.p.=234°–237° C., IR: δ(C-H)>C=C<(-trans)960 cm$^{-1}$; NMR (CF$_3$COOD): vinylic protons $\delta_{H\beta}$=7.34(d), $\delta_{H\alpha}$=8.53(d) p.p.m., $J_{H\alpha H\beta}$=16 Hz;
- 6-carboxy-3-propyl-2-trans-(3'-methyl-styryl)-chromone, m.p.=246°–247° C., IR (KBr): δ(C-H) C=C) (trans) 960 cm$^{-1}$; NMR (CF$_3$COOD): vinylic protons $\delta_{H\beta}$=7.54(d), $\delta_{H\alpha}$=8.36(d) p.p.m., $J_{H\alpha H\beta}$=16 Hz;
- 6-carboxy-3-propyl-2-trans-(4'-methyl-styryl)-chromone, m.p.=266°–267° C.;
- 6-carboxy-3-propyl-2-trans-(2'-ethyl-styryl)-chromone, m.p.=232°–233° C.;
- 6-carboxy-3-propyl-2-trans-(2'-methoxy-styryl)-chromone, m.p.=263°–264° C., IR: δ(C-H)>C=C<(-trans)965 cm$^{-1}$; NMR (CF$_3$COOD): vinylic protons $\delta_{H\beta}$=7.67(d), $\delta_{H\alpha}$=8.4(d) p.p.m., $J_{H\alpha H\beta}$=16 Hz;
- 6-carboxy-3-propyl-2-trans-(2'-ethoxy-styryl)-chromone, m.p.=270°–271° C., IR: δ(C-H)>C=C<(-trans)960 cm$^{-1}$; NMR (CF$_3$COOD): vinylic protons $\delta_{H\beta}$=8.00(d), $\delta_{H\alpha}$=8.50(d) p.p.m., $J_{H\alpha H\beta}$=16 Hz;
- 6-carboxy-3-propyl-2-trans-(3'-methoxy-styryl)-chromone, m.p.=231°–232° C., IR: δ(C-H)>C=C<(-trans)950 cm$^{-1}$; NMR (CF$_3$COOD): vinylic protons $\delta_{H\beta}$=7.33(d), $\delta_{H\alpha}$=7.86(d) p.p.m., $J_{H\alpha H\beta}$=15.5 Hz;
- 6-carboxy-3-propyl-2-trans-(4'-methoxy-styryl)-chromone;
- 6-carboxy-3-propyl-2-trans-(2',5'-dimethyl-styryl)-chromone;
- 6-carboxy-3-propyl-2-trans-(2'-fluoro-styryl)-chromone, m.p.=254°–255° C., IR: δ(C-H)>C=C<(-trans)970,960 cm$^{-1}$; NMR (CF$_3$COOD): vinylic protons $\delta_{H\beta}$=7.84(d), $\delta_{H\alpha}$=8.62(d) p.p.m., $J_{H\alpha H\beta}$=16 Hz;

6-carboxy-3-propyl-2-trans-(4'-fluoro-styrly)-chromone, m.p.=295°-297° C., IR: δ(C-H)>C=C<(trans)960 cm$^{-1}$; NMR (CF$_3$COOD): vinylic protons δ$_{H\beta}$=7.44(d), δ$_{H\alpha}$=8.27(d) p.p.m., J$_{H\alpha H\beta}$=16 Hz;

6-carbomethoxy-3-propyl-2-trans-(2'-methyl-styryl)-chromone, m.p. 139°-141° C.

EXAMPLE 4

By proceeding according to Example 3 and starting frrom methyl 3-butyryl-4-hydroxy-benzoate, the following compounds were prepared:

6-carboxy-3-ethyl-2-trans-styryl-chromone, m.p.=282°-284° C., IR: δ(C-H)>C=C<(trans)960 cm$^{-1}$; NMR (CF$_3$COOD): vinylic protons δ$_{H\beta}$=7.43(d), δ$_{H\alpha}$=8.16(d) p.p.m., J$_{H\alpha H\beta}$=15.5 Hz;

6-carboxy-3-ethyl-2-trans-(2'-methyl-styryl)-chromone, m.p.=270°-271° C., IR: δ(C-H)>C=C<(trans)960 cm$^{-1}$; NMR (CF$_3$COOD): vinylic protons δ$_{H\beta}$=7.27(d), δ$_{H\alpha}$=8.38(d) p.p.m., J$_{H\alpha H\beta}$=16 Hz;

6-carboxy-3-ethyl-2-trans-(3'-methyl-styryl)-chromone;

6-carboxy-3-ethyl-2-trans-(4'-methyl-styryl)-chromone;

6-carboxy-3-ethyl-2-trans-(2'-ethyl-styryl)-chromone;

6-carboxy-3-ethyl-2-trans-(2'-methoxy-styryl)-chromone, m.p.=280°-281° C., IR: δ(C-H)>C=C<(trans)970 cm$^{-1}$; NMR (CF$_3$COOD): vinylic protons δ$_{H\beta}$=7.81(d), δ$_{H\alpha}$=8.69(d) p.p.m., J$_{H\alpha H\beta}$=15.5 Hz;

6-carboxy-3-ethyl-2-trans-[2'-(2-ethoxyethoxy)-styryl]-chromone, m.p.=225°-227° C., IR: δ(C-H)>C=C<(trans)955 cm$^{-1}$; NMR (CF$_3$COOD): vinylic protons δ$_{H\beta}$=7.62(d), δ$_{H\alpha}$=8.55(d) p.p.m., J$_{H\alpha H\beta}$=16 Hz;

6-carboxy-3-ethyl-2-trans-(2',5'-dimethyl-styryl)-chromone.

EXAMPLE 5

By proceeding according to Examples 3 and 4 and using the suitable heterocyclic aldehydes, the following compounds were obtained:

6-carboxy-3-ethyl-2-trans-[β-(2'-thienyl-5'-methyl)-vinyl]-chromone;

6-carboxy-3-ethyl-2-trans-[β-(2'-furyl-5'-methyl)-vinyl]-chromone;

6-carboxy-3-ethyl-2-trans-[β-(2'-pyridyl-6'-methyl)-vinyl]-chromone;

6-carboxy-3-ethyl-2-trans-[β-(2'-thienyl)-vinyl]-chromone, m.p.=268°-270° C., 6-carboxy-3-ethyl-2-trans-[β-(2'-thienyl)-vinyl]-chromone, m.p.=268-270°C, IR: δ (C-H) C=C trans 960 cm$^{-1}$; NMR (DMSOd$_6$-CDCl$_3$ 50:50): vinylic protons 6-carboxy-3-ethyl-2-trans-[β-(2'-pyridyl)-vinyl]-chromone, m.p.=283°-286° C.;

IR (KBr): δ(C-H) C=C trans 960 cm$^{-1}$; NMR (CF$_3$COOD): vinylic protons δ$_{H\alpha+H\beta}$=7.73(s);

6-carboxy-3-propyl-2-trans-[β-2'-furyl)-vinyl]-chromone, m.p.=220°-222° C.; IR (KBr): δ(C-H) C=C trans 955 cm$^{-1}$; NMR (CF$_3$COOD): vinylic protons δ$_{H\beta}$=7.38(d), δ$_{H\alpha}$=8.14(d) p.p.m., J$_{H\alpha H\beta}$=15 Hz;

6-carboxy-3-propyl-2-trans-[β-(2'-thienyl)-vinyl]-chromone, m.p.=243°-245° C., IR: δ(C-H) C=C trans 940 cm$^{-1}$; NMR (CF$_3$COOC): vinylic protons δ$_{H\beta}$=7.24(d), δ$_{H\alpha}$=8.51(d) p.p.m., J$_{H\alpha H\beta}$=15 Hz;

6-carboxy-3-propyl-2-trans-[β-(2'-pyridyl)-vinyl]-chromone, m.p.=278°-280° C., IR: δ(C-H) C=C trans 955 cm$^{-1}$; NMR (CF$_3$COOD): vinylic protons δ$_{H\alpha+H\beta}$=7.99 (s);

6-carboxy-3-propyl-2-trans-[β-(3'-pyridyl)-vinyl]-chromone, m.p.=308°-309° C.; IR: δ(C-H) C=C trans 960 cm$^{-1}$; NMR (CF$_3$COOD): vinylic protons δ$_{H\beta}$=7.74(d), δ$_{H\alpha}$=8.06(d) p.p.m., J$_{H\alpha H\beta}$=16 Hz;

6-carboxy-3-propyl-2-trans-[β-(2'-furyl-5'-methyl)-vinyl]-chromone, m.p.=244°-247° C.; IR (KBr): δ(C-H) C=C trans 950 cm$^{-1}$; NMR (CF$_3$COOD): vinylic protons δ$_{H\beta}$=7.32(d), δ$_{H\alpha}$=8.18(d) p.p.m., J$_{H\alpha H\beta}$=16 Hz;

6-carboxy-3-propyl-2-trans-[β-(2'-pyridyl-6'-methyl)-vinyl]-chromone;

6-carboxy-3-propyl-2-trans-[β-(2'-thienyl-5'-methyl)-vinyl]-chromone.

EXAMPLE 6 g 38 of (2-hydroxy-5-carbo-ethoxy-benzoyl)-trans-cinnamoyl-methane, m.p.=138°-140° C., prepared by proceeding according to Example 1 starting from methyl 3-acetyl-4-hydroxy-benzoate and trans-cinnamoyl chloride, were dissolved in dioxane (400 ml) and dimethylformamide (80 ml) and reacted with allyl bromide (25 ml) in the presence of anhydrous K$_2$CO$_3$ (32.4 g) at 80° C. under stirring for 20 hours. After cooling, the reaction mixture was diluted with water and ice and acidified with citric acid. The precipitate was filtered and washed with water. After crystallization from CH$_2$Cl$_2$-ethyl acetate, 6-carbomethoxy-3-allyl-2-trans-styryl-chromone (23 g), m.p.=215°-217° C. was obtained and treated with a solution of 1% KOH (450 ml) in 95% ethanol under reflux for 30 minutes. After cooling, the solution was acidified with 23% HCl to pH=4 and the precipitate was filtered and washed with ethanol and water until neutral so obtaining 6-carboxy-3-allyl-2-trans-styryl-chromone (20.2 g), m.p.=270°-273° C., IR: δ(C-H)>C=C<(trans)955 cm$^{-1}$; NMR (CF$_3$COOD): vinylic protons δ$_{H\beta}$=7.45(d), δ$_{H\alpha}$=8.21(d) p.p.m., J$_{H\alpha H\beta}$=16 Hz.

By proceeding analogously and starting from the suitable substituted cynnamoyl chlorides, the following compounds were obtained:

6-carboxy-3-allyl-2-trans-(2'-methyl-styryl)-chromone, m.p.=267°-269° C.; IR (KBr): δ(C-H) C=C trans 960 cm$^{-1}$; NMR (DMSO d6-CDCl$_3$50:50): vinylic protons δ$_{H\beta}$=7.06(d), δ$_{H\alpha}$=8.87(d) p.p.m., J$_{H\alpha H\beta}$=16 Hz;

6-carboxy-3-allyl-2-trans-(3'-methyl-styryl)-chromone;

6-carboxy-3-allyl-2-trans-(4'-methyl-styryl)-chromone;

6-carboxy-3-allyl-2-trans-(2'-ethyl-styryl)-chromone;

6-carboxy-3-allyl-2-trans-(3'-methoxy-styryl)-chromone;

6-carboxy-3-allyl-2-cis-styryl-chromone;

6-carboxy-3-allyl-2-cis-(2'-methyl-styryl)-chromone.

EXAMPLE 7 g 20 of 5-carbomethoxy-2-benzyloxy-acetophenone, m.p.=86°-88° C. dissolved in methylene chloride (ml 200) were reacted with bromine (9.8 g) at 10° C. for 15 minutes. After treatment with 10% sodium sulphite and water, the organic phase was evaporated to dryness The residue, crystallized from isopropyl ether, gave 5-carbomethoxy-2-benzyloxy-ω-bromo-acetophenone (17 g), m.p.=84°-86° C., which was dissolved in dimethylformamide (85 ml) and reacted with anhydrous potassium acetate (5.6 g) at 50° C. for 2 hours. After cooling, and dilution with water, the precipitate was filtered and washed with cold methanol so obtaining 5-carbomethoxy-2-benzyloxy-ω-acetoxy-acetophenone (12.9 g), m.p.==86°-87° C., which was dissolved in tetrahydrofuran (40 ml) and ethanol (20 ml); few drops of concentrated HCl were added and then the solution was hydrogenated at atmospheric pressure and room temperature in the presence of 5% Pd/C(2.5g) to the theoretical hydrogen consumption. The mixture was filtered to remove the catalyst and the organic solution was evaporated to dryness so obtaining crude 5-carbomethoxy-2-hydroxy-ω-acetoxy-acetophenone (9.2 g), which was dissolved in dioxane (20 ml) and pyridine (10 ml) and reacted with trans-cinnamoyl-chloride (9.4 g) at room temperature for 8 hours. The reaction mixture was diluted with water and acidified to pH 4. The precipitate was filtered, dried and dissolved in methylethyl-ketone (100 ml); anhydrous $K_2CO_3$ (9.3 g) was added and the mixture was vigorously stirred under reflux for 5 hours. After cooling, the mixture was diluted with hexane (150 ml) and filtered. The collected product was treated with acetic acid (40 ml) and 57% HI (10 ml) under reflux for 4 hours. After cooling, the precipitate was filtered, washed with acetic acid and then with water until neutral; the obtained 6-carboxy-2-trans-styryl-3-hydroxy-chromone (6.1 g), [m.p.>320° C. (dec.), Mass Spectrum: m/e 308 (M+), m/e 291, m/e 278, m/e 263, m/e 231, m/e 165, m/e 143], was dissolved in dimethylformamide (120 ml) and reacted with ethyl iodide (5.1 ml) in the presence of anhydrous $K_2CO_3$ (8.4 g) at 50° C. overnight. After cooling the mixture was diluted with water, filtered, washed with water and crystallized from methanol so obtaining 6-carbethoxy-3-ethoxy-2-trans-styryl-chromone (4.65 g), m.p.=126°-128° C., which was hydrolyzed with a solution of 1% KOH (68.5 ml) in 95% ethanol under reflux for 30 minutes. After cooling, the product was acidified with 23% HCl, filtered and washed until neutral with water so obtaining 6-carboxy-3-ethoxy-2-trans-styryl-chromone (3.15 g), m.p.=252°-254° C., IR: δ(C-H)>C=C<(trans)955 cm$^{-1}$, NMR (CF$_3$COOD):vinylic protons $\delta_{H\beta}$=7.56(d), $\delta_{H\alpha}$=8.19(d) p.p.m., $J_{H\alpha H\beta}$=16 Hz.

By proceeding analogously the following compounds were prepared:
 6-carboxy-3-ethoxy-2-trans-(α-methyl-styryl)-chromone;
 6-carboxy-3-butoxy-2-trans-styryl-chromone, m.p.=192°-194° C., IR: δ(C-H) C=C trans 960 cm$^{-1}$;
 6-carboxy-3-ethoxy-2-trans-(2'-chloro-styryl)-chromone;
 6-carboxy-3-ethoxy-2-trans-(4'-fluoro-styryl)-chromone;
 6-carboxy-3-ethoxy-2-cis-(2'-methyl-styryl)-chromone;
 6-carboxy-3-ethoxy-2-cis-styryl-chromone.

EXAMPLE 8 g 20 of 5-carbomethoxy-2-hydroxy-ω-acetoxy-acetophenone (20 g) obtained by proceeding according to Example 7, were heated under reflux with acetic anhydride (40 ml) in the presence of sodium acetate (8 g). The obtained product was diluted with water and ice, extracted with ethyl acetate. The organic phase was washed with 5% $Na_2CO_3$ and then with water and evaporated to dryness under vacuum so obtaining crude 6-carbomethoxy-3-acetoxy-2-methyl-chromone (22.5 g), which was treated with acetic acid (90 ml) and concentrated HCl (45 ml) under reflux for 4 hours. After cooling, the mixture was diluted with water (100 ml), filtered and washed with water until neutral and then with hot ethanol so obtaining 6-carboxy-3-hydroxy-2-methyl-chromone (13.5 g), which was reacted with ethyl iodide (28.8 g) in dimethylformamide (80 ml) in the presence of anhydrous $K_2CO_3$ at 50° C. for 20 hours. The reaction mixture was diluted with water, filtered and crystallized from methanol to give 6-carbethoxy-3-ethoxy-2-methyl-chromone (10.3 g), which was reacted with benzaldehyde (4.95 g) in methanol (50 ml) containing sodium methylate (2.4 g) at room temperature for 20 hours.

The obtained precipitate was filtered, washed with methanol and then with water to obtain 6-carbethoxy-3-ethoxy-2-trans-styryl-chromone (10.8 g), m.p.=126°-128° C. which was hydrolized with a solution of 1% KOH (185 ml) in 95% ethanol at the reflux temperature for 30 minutes.

After cooling, the mixture wa acidified with 23% HCl and the precipate was filtered and washed with ethanol and water, so obtaining 6-carboxy-3-ethoxy-2-trans-styryl-chromone (8.8 g), m.p.=252°-254° C., IR:δ(C-H)>C=C<(trans)955 cm$^{-1}$; NMR (CF$_3$COOD): vinylic protons $\delta_{H\beta}$=7.56(d), $\delta_{H\alpha}$=8.19(d) p.p.m., $J_{H\alpha H\beta}$=16 Hz.

By proceeding analogously and using the suitable aromatic aldehydes, the following compounds were prepared:
 6-carboxy-3-propoxy-2-trans-styryl-chromone, m.p.=210°-212° C., IR: δ(C-H)>C=C<(-trans)960 cm$^{-1}$; NMR (CF$_3$COOD):vinylic protons $\delta_{H\beta}$=7.49(d), $\delta_{H\alpha}$=8.14(d) p.p.m., $J_{H\alpha H\beta}$=16 Hz;
 6-carboxy-3-butoxy-2-trans-styryl-chromone, m.p.=192°-194° C., IR: δ(C-H)>C=C<(-trans(960 cm$^-$;
 6-carboxy-3-isopropoxy-2-trans-styryl-chromone;
 6-carboxy-3-isopropoxy-2-trans-(2'-methyl-stryryl)-chromone;
 6-carboxy-3-ethoxy-2-trans-(2'-methyl-styryl)-chromone;
 6-carboxy-3-ethoxy-2-trans-(3'-methyl-styryl)-chromone;
 6-carboxy-3-ethoxy-2-trans-(4'-methyl-styryl)-chromone;
 6-carboxy-3-ethoxy-2-trans-(2'-ethyl-styryl)-chromone;
 6-carboxy-3-ethoxy-2-trans-(3'-methoxy-styryl)-chromone;
 6-carboxy-3-butoxy-2-trans-(2'-methyl-styryl)-chromone;
 6-carboxy-3-butoxy-2-trans-(3'-methyl-styryl)-chromone;
 6-carboxy-3-butoxy-2-trans-(4'-methyl-styryl)-chromone;
 6-carboxy-3-butoxy-2-trans-(2'-ethyl-styryl)-chromone;
 6-carboxy-3-butoxy-2-trans-(3'-methoxy-styryl)-chromone;
 6-carboxy-3-isobutoxy-2-trans-styryl-chromone;

6-carboxy-3-isobutoxy-2-trans-(2'-methyl-styryl)-chromone.

EXAMPLE 9

By proceeding according to Example 8 and using the suitable heterocyclic aldehydes, the following compounds were obtained:

6-carboxy-3-ethoxy-2-trans-[β-(2'-furyl)-vinyl])-chromone;
6-carboxy-3-ethoxy-2-trans-[β-(2'-thienyl)-vinyl]-chromone;
6-carboxy-3-ethoxy-2-trans-[β-(2'-pyridyl)-vinyl]-chromone;
6-carboxy-3-butoxy-2-trans-[β-(2'-furyl-5'-methyl)-vinyl]-chromone;
6-carboxy-3-butoxy-2-trans-[β-(2'-thienyl)-vinyl]-chromone;
6-carboxy-3-butoxy-2-trans-[β-(2'-pyridyl)-vinyl]-chromone;
6-carboxy-3-isobutoxy-2-trans-[β-(2'pyridyl)-vinyl]-chromone;
6-carboxy-3-ethoxy-2-trans-[β-(2'-furyl-5'-methyl)-vinyl]-chromone;
6-carboxy-3-ethoxy-2-trans-[β-(2'-pyridyl-6'-methyl)-vinyl]-chromone;
6-carboxy-3-ethoxy-2-trans-[β-(2'thienyl-5'-methyl)-vinyl]-chromone.

EXAMPLE 10 g 19 of methyl 3-acetyl-4-hydroxy-benzoate in methanol (250 ml) were reacted with cinnamic aldehyde (37 g) in the presence of sodium methylate (14 g) at room temperature for 18 hours. After concentration to half volume, the reaction mixture was acidified with acetic acid and the precipitate was filtered so obtaining methyl 3-(cinnamylydene-acetyl)-4-hydroxy-benzoate(9g), m.p.=128°–130° C., which was dissolved in ethanol (470 ml) and water (70 ml) containing NaOH (23.5 g); the solution was then reacted with 36% $H_2O_2$ at room temperature for 20 hours. After acidification, the precipitate was filtered and washed with water and hot ethanol to obtain 6-carboxy-3-hydroxy-2-trans-styryl-chromone (4.5 g), m.p.=320° C. (dec), which was treated with propyl bromide (2 g) in dimethylformamide (45 ml) in the presence of anhydrous $K_2CO_3$ (6 g) at 50° C. overnight. After dilution with water, filtration and washing with methanol, 6-carbopropoxy-3-propoxy-2-trans-styryl-chromone (5.2 g), m.p.=95°–97° C. was obtained which was then hydrolyzed with a solution of 1% KOH (77 ml) in 95% ethanol at the reflux temperature in 30 minutes. After cooling, the mixture was acidified with 23% HCl; the precipitate was filtered, then washed with ethanol and water; 6-carboxy-3-propoxy-2-trans-styryl-chromone (4.1 g), m.p.=210°–212° C.; IR: δ(C-H)>C=C<(-trans)960 cm$^{-1}$; NMR (CF$_3$COOD):vinylic protons $\delta_{H\beta}=7.49(d)$, $\delta_{H\alpha}=8.14(d)$ p.p.m., $J_{H\alpha H\beta}=16$ Hz was obtained.

By proceeding analogously the following compounds were prepared:
6-carboxy-3-ethoxy-2-trans-styryl-chromone, m.p.=252°–254° C., IR: δ(C-H)>C=C<(-trans)955 cm$^{-1}$; NMR (CF$_3$COOD):vinylic protons $\delta_{H\beta}=7.56(d)$, $\delta_{H\alpha}=8.19(d)$ p.p.m., $J_{H\alpha H\beta}=16$ Hz;
6-carboxy-3-butoxy-2-trans-styryl-chromone, m.p.=192°–194° C., IR: δ(C-H)>C=C<(-trans)960 cm$^{-1}$;
6-carboxy-3-isopropoxy-2-trans-styryl-chromone;
6-carboxy-3-isobutoxy-2-trans-styryl-chromone.

EXAMPLE 11 g 12 of 6-carboxy-3-propoxy-2-trans-styryl-chromone were reacted with thionyl chloride (4 ml) in dichloroethane (80 ml) at the reflux temperature for 2 hours. After cooling, the reaction mixture was evaporated to dryness and reacted with an excess of anhydrous ethanol at 50° C. for 1 hour. The mixture was concentrated at small volume and diluted with water to obtain, by filtration, 6-carbethoxy-3-propyl-2-trans-styryl-chromone (9.6 g), m.p.=154°–156° C., IR: δ(C-H) C=C trans 960 cm$^{-1}$; NMR (CDCl$_3$):vinylic protons $\delta_{H\beta}=7.07(d)$, $\delta_{H\alpha}=7.58(d)$ p.p.m., $J_{H\alpha H\beta}=16$ Hz.

By proceeding analogously the following compounds were prepared:
6-carbetoxy-3-propyl-2-trans-(2'-methyl-styryl)-chromone;
6-carbethoxy-3-propyl-2-trans-(3'-methyl-styryl)-chromone;
6-carbethoxy-3-propyl-2-trans-(4'-methyl-styryl)-chromone;
6-carbethoxy-3-propyl-2-trans-(2',5'-dimethyl-styryl)-chromone;
6-carbethoxy-3-propyl-2-trans-[β-(2'-furyl-5'-methyl)-vinyl]-chromone;
6-carbethoxy-3-propyl-2-trans-[β-(2'-thienyl)-vinyl]-chromone;
6-carbethoxy-3-propyl-2-trans-[β-(2'-pyridyl-6'-methyl)-vinyl]-chromone;
6-carbethoxy-3-ethyl-2-trans-styryl-chromone;
6-carbethoxy-3-ethyl-2-trans-[β-(2'-furyl-5'-methyl)-vinyl]-chromone;
6-carbethoxy-3-ethoxy-2-trans-styryl-chromone; m.p. 126°–128° C.;
6-carbethoxy-3-ethoxy-2-trans-[β-(2'-pyridyl)-vinyl]-chromone;
6-carbethoxy-3-ethoxy-2-trans-[β-(2'-pyridyl-6'-methyl)-vinyl]-chromone;
6-carbethoxy-3-allyl-2-trans-styryl-chromone;
6-carbethoxy-3-ethoxy-2-trans-(2'-methyl-styryl)-chromone;
6-carbethoxy-3-ethoxy-2-trans-[β-(2'-furyl-5'-methyl)-vinyl]-chromone;
6-carbethoxy-3-propyl-2-cis-(2'-methyl-styryl)-chromone;
6-carbethoxy-3-propyl-2-cis-styryl-chromone;
6-carbethoxy-3-ethyl-2-cis-styryl-chromone;
6-carbethoxy-3-ethoxy-2-cis-styryl-chromone.

EXAMPLE 12

By proceeding according to Example 11 and using the suitable aliphatic alcohols the isopropyl ester, t-butyl ester, hexyl ester, octyl ester and undecyl ester of the following acids were prepared:
6-carboxy-3-propyl-2-trans-styryl-chromone;
6-carboxy-3-propyl-2-trans-(2'-methyl-styryl)-chromone;
6-carboxy-3-propyl-2-trans-(3'-methyl-styryl)-chromone;
6-carboxy-3-propyl-2-trans-(4'-methyl-stytyl)-chromone;
6-carboxy-3-propyl-2-trans-(2',5'-dimethyl-stytyl)-chromone;
6-carboxy-3-propyl-2-trans-[β-(2'-furyl-5'-methyl)-vinyl]-chromone;

6-carboxy-3-propyl-2-trans-[β-(2'-thienyl)-vinyl]-chromone;
6-carboxy-3-propyl-2-trans-[β-(2'-thienyl-5'-methyl)-vinyl-chromone;
6-carboxy-3-propyl-2-trans-[β-(2'-pyridyl-6'-methyl)-vinyl]-chromone;
6-carboxy-3-ethyl-2-trans-styryl-chromone;
6-carboxy-3-ethyl-2-trans-[β-(2'-pyridyl)-vinyl]-chromone;
6-carboxy-3-ethyl-2-trans-[β-(2'-pyridyl-6'-methyl)-vinyl]-chromone;
6-carboxy-3-ethoxy-2-trans-styryl-chromone;
6-carboxy-3-ethoxy-2-trans-[β-(2'-thienyl)-vinyl]-chromone;
6-carboxy-3-ethoxy-2-trans-[β-(2'-pyridyl-6'-methyl)-vinyl]-chromone;
6-carboxy-3-butoxy-2-trans-styryl-chromone;
6-carboxy-3-allyl-2-trans-styryl-chromone;
6-carboxy-3-ethoxy-2-trans-(2'-methyl-styryl)-chromone;
6-carboxy-3-ethoxy-2-trans-[β-(2'-furyl-5'-methyl)-vinyl]-chromone;
6-carboxy-3-propyl-2-cis-styryl-chromone.

EXAMPLE 13 g 5 of 6-carboxy-3-propyl-2-trans-(2'-methyl-styryl)-chromone were reacted at 100° C. with NaHCO$_3$ (1.25 g) in water (25 ml), working far from the light, until the solution is completed. By cooling the solution to 5° C., a precipitate was obtained, which was then filtered and washed with icy water to give the sodium salt of 6-carboxy-3-propyl-2-trans-(2'-methyl-styryl)-chromone (4.4 g). By proceeding analogously the sodium salts of the following acids were prepared:
2-cis-styryl-chromone;
6-carboxy-3-ethyl-2-cis-styryl-chromone;
6-carboxy-3-ethoxy-2-cis-styryl-chromone;
6-carboxy-3-propyl-2-cis-(2'-methyl-styryl)-chromone;
6-carboxy-3-propyl-2-trans-styryl-chromone;
6-carboxy-3-ethyl-2-trans-styryl-chromone;
6-carboxy-3-ethoxy-2-trans-styryl-chromone;
6-carboxy-3-propyl-2-trans-(3'-methyl-styryl)-chromone;
6-carboxy-3-propyl-2-trans-[β-(2'-thienyl)-vinyl]-chromone;
6-carboxy-3-propyl-2-trans-[β-(2'-furyl-5'-methyl)-vinyl]-chromone;
6-carboxy-3-propyl-2-trans-[β-(2'-pyridyl-6'-methyl)-vinyl]-chromone;
6-carboxy-3-ethoxy-2-trans-[β-(2'-thienyl)-vinyl]-chromone;
6-carboxy-3-ethoxy-2-trans-[β-(2'-pyridyl-6'-methyl)-vinyl]-chromone;
6-carboxy-3-allyl-2-trans-styryl-chromone;
6-carboxy-3-propyl-2-trans-(4'-methyl-styryl)-chromone;
6-carboxy-3-propyl-2-trans-(2',5'-dimethyl-styryl)-chromone;
6-carboxy-3-ethoxy-2-trans-[β-(2'-furyl-5'-methyl)-vinyl]-chromone;
6-carboxy-3-ethoxy-2-trans-(2'-methyl-styryl)-chromone;
6-carboxy-3-propyl-2-trans-[β-(2'-thienyl-5'-methyl)-vinyl]-chromone.

EXAMPLE 14

A mixture of g 3.5 of 6-carboxy-3-propyl-2-trans-(2'-methyl-styryl)-chromone and N-methyl-benzyl-amine (1.6 g) was stirred at 120° C. for 30 minutes. After cooling, ethyl acetate (50 ml) was added and the mixture was left to crystallize under stirring. After filtration and washing with ethyl acetate g 4.1 of the N-methyl-N-benzylammonium salt of 6-carboxy-3-propyl-2-trans-(2'-methyl-styryl)-chromone were obtained. By proceeding analogously the N-methyl-N-benzyl-ammonium salts of the acids listed in Example 13 were prepared.

EXAMPLE 15 g 6.2 of 3-propyl-2-trans-styryl-chromone-6-carbonyl-chloride prepared according to Example 11 were dissolved in dioxane (40 ml) and reacted with 2-diethylamino-ethanol (2ml) in the presence of triethylamine (1 ml) at room temperature for 20 hours. The reaction mixture was diluted with water and filtered. The collected product was dissolved in acetone (200 ml) and treated with the stoichiometric amount of concentrated HCl. The so obtained precipitate was filtered, washed with acetone and dissolved in water. After alkalinization of the aqueous solution with K$_2$CO$_3$ and filtration the diethylaminoethyl ester (4.5 g) of the 6-carboxy-3-propyl-2-trans-styryl-chromone, m.p. = 89°–91° C., IR: $\delta$(C-H)>C=C<(trans) 960 cm$^{-1}$; NMR (CDCl$_3$):vinylic protons $\delta_{H\beta}$=7.10(d), $\delta_{H\alpha}$=7.62(d) p.p.m., $J_{H\alpha H\beta}$=16 Hz was obtained. Analagously, the diethylaminoethyl esters of the following acids were prepared:
6-carboxy-3-propyl-2-trans-(2',5'-dimethyl-styryl)-chromone;
6-carboxy-3-propyl-2-trans-(4'-methyl-styryl)-chromone;
6-carboxy-3-propyl-2-trans-(2'-methyl-styryl)-chromone;
6-carboxy-3-propyl-2-trans-(3'-methyl-styryl)-chromone;
6-carboxy-3-propyl-2-trans-[β-(2'-furyl-5'-methyl)-vinyl]-chromone;
6-carboxy-3-propyl-2-trans-[β-(2'-pyridyl-6'-methyl)-vinyl]-chromone;
6-carboxy-3-propyl-2-trans-[β-(2'-thienyl)-vinyl]-chromone;
6-carboxy-3-ethyl-2-trans-styryl-chromone;
6-carboxy-3-ethoxy-2-trans-styryl-chromone;
6-carboxy-3-ethoxy-2-trans-[β(2'pyridyl)-vinyl]-chromone;
6-carboxy-3-ethoxy-2-trans-[β-(2'-pyridyl-6'-methyl)]-chromone;
6-carboxy-3-ethoxy-2-trans-[β-(2'-furyl-5'-methyl)-vinyl]-chromone;
6-carboxy-3-propyl-2-trans-[β-(2'-thienyl-5'-methyl)-vinyl]-chromone;
6-carboxy-3-ethoxy-2-trans-[β-(2'-thienyl)-vinyl]-chromone;
6-carboxy-3-allyl-2-trans-styryl-chromone;
6-carboxy-3-ethoxy- 2-trans-(2'-methyl-styryl)-chromone;
6-carboxy-3-ethyl-2-styryl-chromone;
6-carboxy-3-ethoxy-2-cis-styryl-chromone;
6-carboxy-3-propyl-2-cis-styryl-chromone;
6-carboxy-3-propyl-2-cis-(2'-methyl-styryl)-chromone.

EXAMPLE 16 g 5 of 6-carbethoxy-3-propyl-2-trans-styryl-chromone, obtained proceeding according to Example 11, were reacted with $P_2S_5$ (3.9 g) in dioxane (100 ml) at the reflux temperature for 3 hours. After cooling, 1N NaOH (75 ml) was cautiously added. The mixture was stirred for 1 hour at room temperature, far from the light, acidified with 2N HCl and filtered. After crystallization from eethyl acetate 6-carboxy-3-propyl-2-trans-styryl-4-thio-chromone (2.7 g) was obtained. By proceeding analogously, the following compounds were prepared:

6-carboxy-3-propyl-2-trans-(2'-methyl-styryl)-4-thio-chromone;
6-carboxy-3-propyl-2-trans-(3'-methyl-styryl)-4-thio-chromone;
6-carboxy-3-ethyl-2-trans-styryl-4-thio-chromone;
6-carboxy-3-allyl-2-trans-styryl-4-thio-chromone;
6-carboxy-3-propyl-2-trans-(2',5'-dimethyl-styryl)-4-thio-chromone;
6-carboxy-3-propyl-2-trans-(4'-methyl-styryl)-4-thio-chromone;
6-carboxy-3-ethoxy-2-trans-styryl-4-thio-chromone;
6-carboxy-3-ethoxy-2-trans-(2'-methyl-styryl)-4-thio-chromone;
6-carboxy-3-ethyl-2-cis-styryl-4-thio-chromone;
6-carboxy-3-propyl-2-cis-styryl-4-thio-chromone;
6-carboxy-3-ethoxy-2-cis-styryl-4-thio-chromone.

We claim:

1. A compound of the formula

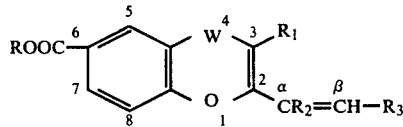

wherein

R is hydrogen or $C_1$–$C_{12}$ alkyl, unsubstituted or substituted by a $C_2$–$C_5$ alkanoyloxy or by a

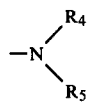

group,
wherein each of $R_4$ and $R_5$ is independently selected from the group consisting of hydrogen and $C_1$–$C_{10}$ alkyl;
$R_1$ is $C_2$–$C_4$ alkyl or $C_3$–$C_4$ alkenyl;
$R_2$ is hydrogen or methyl;
$R_3$ is furyl substituted by a 5'-methyl group or thienyl which is unsubstituted or substituted by a 5'-methyl group;
W is $>C=O$ or $>C=S$, and a pharmaceutically acceptable salt thereof.

2. A pharmaceutical composition suitable for the treatment of allergies, said composition comprising an effective amount of a compound of claim 1 and a pharmaceutically acceptable carrier and/or diluent.

3. A compound of the formula

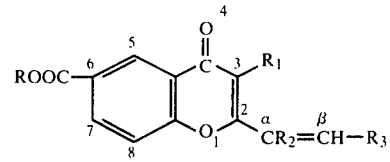

wherein
R is hydrogen or $C_1$–$C_6$ alkyl;
$R_1$ is ethyl, propyl or allyl;
$R_2$ is hydrogen or methyl;
$R_3$ is 2-furyl substituted by a 5'-methyl group or 2-thienyl which is unsubstituted or substituted by a 5'-methyl group; and wherein the vinyl moiety has the trans-configuration, and a pharmaceutically acceptable salt thereof.

4. Pharmaceutical composition of claim 2 wherein said composition contains an effective amount of a compound of claim 3.

5. A compound of the formula

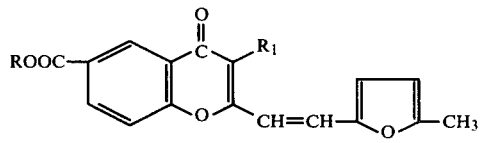

wherein R is hydrogen or $C_1$–$C_{12}$ alkyl, unsubstituted or substituted by a $C_2$–$C_5$ alkanoyloxy or by a

group, wherein each of $R_4$ and $R_5$ is independently selected from the group consisting of hydrogen and $C_1$–$C_{10}$ alkyl;
$R_1$ is $C_2$–$C_4$ alkyl or $C_3$–$C_4$ alkenyl; and a pharmaceutically acceptable salt thereof.

6. Parmaceutical composition of claim 2, wherein said composition contains an effective amount of a compound of claim 5.

7. A method of treating allergic conditions in a patient in need of such treatment, said method comprising administering to said patient a therapeutically effective amount of a compound of claim 1.

8. The method of claim 7, wherein said compound is administered orally.

9. A compound selected from the group consisting of:
6-carboxy-3-propyl-2-trans-[β-(2'-thienyl)-vinyl]-chromone;
6-carboxy-3-propyl-2-trans-[β-(2'-furyl-5'-methyl)-vinyl]-chromone;
6-carboxy-3-propyl-2-trans-[β-(2'-(2'-thienyl-5'-methyl)-vinyl]-chromone; as well as the pharmaceutically acceptable salts thereof.

10. The compound 6-carboxy-3-propyl-2-trans-[β-(2'-furyl-5'-methyl)vinyl]chromone.

11. Method of claim 7, whrein a therapeutically effective amount of a compound of claim 16 is administered to said patient.

* * * * *